United States Patent [19]

Bryce-Smith

[11] Patent Number: 5,792,449
[45] Date of Patent: Aug. 11, 1998

[54] COMPOSITIONS CONTAINING ZINC LINOLEATE FOR THE TREATMENT OF SKIN DISORDERS

[75] Inventor: Derek Bryce-Smith, Reading, Great Britain

[73] Assignee: Kappa Pharmaceuticals Limited, Great Britain

[21] Appl. No.: 640,911

[22] PCT Filed: Oct. 28, 1994

[86] PCT No.: PCT/GB94/02370

§ 371 Date: May 10, 1996

§ 102(e) Date: May 10, 1996

[87] PCT Pub. No.: WO95/13806

PCT Pub. Date: May 26, 1995

[30] Foreign Application Priority Data

Nov. 18, 1993 [GB] United Kingdom .................. 9323808

[51] Int. Cl.$^6$ .................................................. A61K 31/74
[52] U.S. Cl. .................................................. 424/78.02
[58] Field of Search .................................. 424/78.02

[56] References Cited

FOREIGN PATENT DOCUMENTS 2217602  1/1989  United Kingdom .

*Primary Examiner*—Terressa Mosley
*Attorney, Agent, or Firm*—Renner, Otto, Boisselle & Sklar

[57] ABSTRACT

There is disclosed a composition for the treatment of skin disorders comprising zinc linoleate and free linoleic acid in a pharmaceutically acceptable carrier.

11 Claims, No Drawings

COMPOSITIONS CONTAINING ZINC LINOLEATE FOR THE TREATMENT OF SKIN DISORDERS

This invention concerns a composition containing zinc for the treatment of skin disorders.

Conventional zinc containing creams and ointments comprise zinc in the form of zinc oxide.

Zinc oxide is a form of zinc highly insoluble in water, lipids and non-polar solvents and is thus merely suspended in a pharmaceutical carrier to produce a white ointment or cream which is poorly absorbed into the skin leaving unsightly deposits on the skin after use.

The present invention overcomes, at least to some extent, the problems aforesaid.

According to the present invention there is provided a composition for the treatment of skin disorders comprising zinc linoleate and free linoleic acid in a pharmaceutically acceptable carrier.

Zinc linoleate is a colourless and fat soluble form of zinc which is readily absorbed into the skin.

Since it is known that slightly acidic compositions are better absorbed by the skin than neutral or alkaline preparations, free linoleic acid is included in the composition to adjust the pH of the composition to around pH 5.5.

The composition may comprise a zinc ion content of 0.1 to 8.5%, and preferably between 1 and 5%.

The composition may comprise a free linoleic acid content of 0.1 to 50%.

The composition may also comprise zinc oleate, zinc oxide, zinc salts of conjugated isomers of linoleic acid, water and an emulsifying agent.

The composition may also comprise an antioxidant, for example, vitamin E or vitamin A.

The composition may also comprise vitamin $D_3$ or any other additive known to have properties beneficial to any skin condition.

The composition may be used topically to relieve the symptoms of a variety of skin conditions, for example, eczema, dermatitis, psoriasis, acne vulgaris, nappy rash.

The composition may also comprise an antibacterial constituent, for example, zinc iodate, potassium iodate, an iodophor or cetylpyrididium chloride. Such a composition is envisaged to be of particular use for the treatment of minor cuts and abrasions as well as more severe leg and other cutaneous ulcers.

The composition may also comprise a minor proportion of copper ions, preferably in the form of copper linoleate.

The composition may also comprise a local anaesthetic, for example, lignocaine. Such a preparation would give rapid symptomatic relief of itching and/or pain.

The pharmaceutically acceptable carrier may comprise emulsifying ointment BP or any other suitable carrier, for example, soft/hard paraffin.

The composition may be applied topically to the skin in the form of a cream or ointment, or via a pad or bandage pre-soaked in the composition, or by any other mode of administration capable of delivering an effective amount of composition to the site of injury.

The composition may vary in consistency from a cream to an ointment by varying its water content.

It is envisaged that a zinc linoleate cream according to the present invention may be used in cosmetics and sunscreen lotions.

According to a second aspect of the invention there is provided a method of manufacture of a composition for the treatment of skin disorders comprising zinc linoleate and free linoleic acid in a pharmaceutically acceptable carrier.

A method of manufacture may comprise mixing zinc oxide in a suitable carrier, for example, emulsifying ointment BP, adding linoleic acid and heating with stirring to a temperature sufficient to convert essentially all the zinc oxide into zinc linoleate whilst leaving sufficient free linoleic acid to maintain a slightly acidic pH of the composition upon cooling.

An example of this method of manufacture of the composition of the present invention comprises stirring together 15 g zinc oxide with 250 g emulsifying ointment BP and warming until fluid. 227 ml of linoleic acid is then stirred into the mixture which is heated to 70° C. until the liquid turns pale yellow and is only slightly turbid. The mixture is then left to cool with stirring to give the composition of the present invention.

The linoleic acid used may not be pure linoleic acid but may comprise 68% linoleic acid, 22% oleic acid and 10% conjugated isomers of linoleic acid, (as manufactured by Hercules, USA).

Part of the linoleic acid may be in the form of a glyceride.

The amount of free linoleic acid present in the composition may be varied by varying the amount of zinc oxide present.

Water may be added to the composition before cooling to vary the consistency of the composition. This step requires vigorous stirring in order to emulsify the mixture, for example, 100 ml of water was added to the mixture disclosed above, whilst warm, with vigorous agitation prior to cooling to give a softer product.

Alternatively, the composition may be manufactured by the method of dispersing pre-formed zinc linoleate and free linoleic acid in a suitable carrier.

A small scale test on 5 individuals suffering form dermatitis showed that application of the composition of the present invention rapidly relieved all symptoms thereof. Itching ceased within ten minutes. In another test, the ointment of the present invention was used with four individuals suffering from psoriasis. All showed considerable benefit within two weeks.

I claim:

1. A composition for the treatment of skin disorders comprising zinc linoleate and free linoleic acid in a pharmaceutically acceptable carrier, wherein the composition has a zinc ion content of 0.1 to 8.5%.

2. A composition according to claim 1 having a pH of around 5.5.

3. A composition according to claim 1 having a free lineolic acid content of 0.1 to 50%.

4. A composition according to claim 1 further comprising one or more of zinc oleate, zinc oxide, zinc salts of conjugated isomers of linoleic acid, an antioxidant (for example vitamin E or vitamin A), vitamin $D_3$, an antibacterial constituent (for example, zinc iodate, potassium iodate, an iodophor or cetylpyridinium chloride), a minor proportion of copper ions (preferably in the form of copper linoleate) and a local anaesthetic (for example, lignocaine).

5. A composition according to claim 1 wherein the pharmaceutically acceptable carrier comprises an emulsifying ointment.

6. A composition according to claim 5 wherein the carrier includes water.

7. A composition according to claim 1 included in a cosmetic or sunscreen lotion.

8. A method of manufacture of a composition for the treatment of skin disorders comprising zinc linoleate and free linoleic acid in a pharmaceutically acceptable carrier comprising the steps of mixing zinc oxide in a suitable carrier, adding linoleic acid and heating with stirring to a temperature sufficient to convert essentially all the zinc oxide into zinc linoleate whilst leaving sufficient free linoleic acid to maintain a slightly acid pH of the composition upon cooling, wherein the composition has a zinc ion content of 0.1 to 8.5%.

9. A method of manufacture of a composition for the treatment of skin disorders comprising zinc linoleate and free linoleic acid in a pharmaceutically acceptable carrier comprising dispersing pre-formed zinc linoleate and free linoleic acid in said carrier, wherein the composition has a zinc ion content of 0.1 to 8.5%.

10. A composition according to claim 1 wherein the pharmaceutically acceptable carrier comprises soft paraffin.

11. A composition according to claim 1 wherein the pharmaceutically acceptable carrier comprises hard paraffin.

* * * * *